US009902689B2

(12) United States Patent
Ott et al.

(10) Patent No.: US 9,902,689 B2
(45) Date of Patent: Feb. 27, 2018

(54) PROCESS FOR PREPARING ALKANESULFONIC ACIDS FROM SULFUR TRIOXIDE AND AN ALKANE

(71) Applicant: Grillo Chemie GmbH, Duisburg (DE)

(72) Inventors: Timo Ott, Duisburg (DE); Ingo Biertümpel, Duisburg (DE); Klaus Bunthoff, Duisburg (DE); Alan Richards, Palm City, FL (US)

(73) Assignee: Grillo Chemie GMBH, Duisburg (DE)

( * ) Notice: Subject to any disclaimer, the term of this patent is extended or adjusted under 35 U.S.C. 154(b) by 0 days.

(21) Appl. No.: 15/036,215

(22) PCT Filed: Nov. 13, 2014

(86) PCT No.: PCT/EP2014/074500
§ 371 (c)(1),
(2) Date: May 12, 2016

(87) PCT Pub. No.: WO2015/071365
PCT Pub. Date: May 21, 2015

(65) Prior Publication Data
US 2016/0289176 A1    Oct. 6, 2016

(30) Foreign Application Priority Data

Nov. 13, 2013 (EP) .................................... 13192729

(51) Int. Cl.
*C07C 309/00*    (2006.01)
*C07C 303/06*    (2006.01)

(52) U.S. Cl.
CPC .................................. *C07C 303/06* (2013.01)

(58) Field of Classification Search
CPC ............................. C07C 303/06; C07C 309/04
See application file for complete search history.

(56) References Cited

U.S. PATENT DOCUMENTS

| | | | |
|---|---|---|---|
| 2,493,038 A | 1/1950 | Snyder | |
| 2,619,507 A | 11/1952 | Jones et al. | |
| 4,680,095 A | 7/1987 | Wheaton | |
| 4,910,335 A * | 3/1990 | Wheaton | .............. C07C 303/44 |
| | | | 562/124 |
| 5,304,360 A | 4/1994 | Lane et al. | |
| 7,282,603 B2 | 10/2007 | Richards | |
| 2005/0070614 A1 | 3/2005 | Richards | |
| 2007/0282151 A1 | 12/2007 | Richards | |
| 2008/0161591 A1 * | 7/2008 | Richards | ................ C01B 15/08 |
| | | | 558/44 |
| 2016/0289181 A1 | 10/2016 | Ott | |

FOREIGN PATENT DOCUMENTS

| | | |
|---|---|---|
| EP | 1558353 B1 | 6/2016 |
| WO | 2004041399 A2 | 5/2004 |
| WO | 2005069751 A2 | 8/2005 |
| WO | 2007136425 A2 | 11/2007 |
| WO | WO2007136425 A2 | 11/2007 |
| WO | 2015071351 A1 | 5/2015 |
| WO | 2015071365 A1 | 5/2015 |
| WO | 2015071371 A1 | 5/2015 |
| WO | 2015071455 A1 | 5/2015 |

OTHER PUBLICATIONS

U.S. Appl. No. 15/036,215, Translation of foreign patent document filed Jan. 10, 2017.*
Willstätter et al., "On the Knowledge of Caro's Acid", Chemical Laboratory of The Schweizerisches Polytechnikum of Zurich, 15 pages (Apr. 1, 1909).
Korth et al, "Direct Spectroscopic Detection of Sulfonyloxyl Radicals and First Measurements of Their Absolute Reactivities1a", J. Phys. Chem. 94, 8835-8839 (1990).

* cited by examiner

*Primary Examiner* — Yevegeny Valenrod
*Assistant Examiner* — Blaine G Doletski
(74) *Attorney, Agent, or Firm* — Christensen, Fonder, Dardi & Herbert PLLC; Curtis Herbert

(57) ABSTRACT

A process for preparing alkanesulfonic acids from sulfur trioxide and an alkane, wherein sulfur trioxide, the alkane and dialkylsulfonoyi peroxide (DASP) react as components, characterized in that the following steps are performed: a) sulfur trioxide is charged in a high-pressure reactor in a condensed phase; b) a temperature of at least 25° C. is set; c) the gaseous alkane is introduced to the high-pressure reactor until a pressure of at least 10 bar is reached; d) dialkylsulfonoyi peroxide (DASP) is added; and e) after a duration of at least 5 hours, the produced alkanesulfonic acid is withdrawn.

10 Claims, No Drawings

PROCESS FOR PREPARING ALKANESULFONIC ACIDS FROM SULFUR TRIOXIDE AND AN ALKANE

CROSS REFERENCE TO RELATED APPLICATIONS

This application is a national stage filing of PCT Application Number PCT/EP2014/074500 filed Nov. 13, 2014, which claims priority to European Patent Application Number 13192729.5 filed Nov. 13, 2013, both of which are hereby incorporated herein by reference.

TECHNICAL FIELD

The present invention relates to a process for preparing alkanesulfonic acids from sulfur trioxide and an alkane.

BACKGROUND

Alkanesulfonic acids are organic acids that can reach a similar acid strength as that of inorganic mineral acids, for example, sulfuric acid. However, in contrast to usual mineral acids such as sulfuric and nitric acids, the sulfonic acids are non-oxidizing and do not give off vapors that are harmful to health, as can be observed with hydrochloric and nitric acids. Further, many sulfonic acids, for example, methanesulfonic acid, are biologically degradable. The applications of sulfonic acids are many, for example, in cleaning agents, surfactants, as catalysts, and in organic synthesis, pharmaceutical chemistry, for example, as protective groups. The salts of sulfonic acids are employed, for example, as surfactants, for example, sodium dodecylsulfonate, or in the electroplating industry, especially as tin, zinc, silver, lead and indium, but also other metal alkylsulfonates. The very high solubility of alkyl sulfonates plays an important role, in particular. Further, no harmful gases are formed in electrolysis, and the use of toxic compounds, for example, cyanide, which is common in many cases, is dispensed with.

The structurally simplest representative of alkanesulfonic acids is methanesulfonic acid. U.S. Pat. No. 2,493,038 describes the preparation of methanesulfonic acid from $SO_3$ and methane. US 2005/0070614 A1 and US 2008/0161591 A1 describe further methods for preparing methanesulfonic acid, and its application. The methods known in the prior art are in part complicated, cost-intensive, and lead to undesirable products because of the harsh conditions.

SUMMARY OF THE INVENTION AND DETAILED DESCRIPTION

The reaction conditions in conventional processes of alkanesulfonic acid production can result in undesirable side products, which even manifest themselves as disturbing inhibitors in the production of alkanesulfonic acids. This may lead to termination of the actual reaction for preparing the alkanesulfonic acid, but also to impurities, formation of side products and poor yields, based on sulfur trioxide and methane.

It is the object of the present invention to provide a process that avoids the above mentioned drawbacks.

The object of the invention is achieved by a process for preparing alkanesulfonic acids from sulfur trioxide and an alkane, wherein sulfur trioxide, the alkane and dialkylsulfonyl peroxide (DASP) react as components. The process is characterized in that the following steps are performed:

a) sulfur trioxide or a solution thereof in a solvent is charged in a high-pressure reactor in a condensed phase;

b) a temperature of at least 25° C. is set;

c) the gaseous alkane is introduced to the high-pressure reactor until a pressure of at least 10 bar is reached;

d) dialkylsulfonoyl peroxide (DASP) is added; and e) after a duration of at least 5 hours, the produced alkanesulfonic acid is withdrawn.

Advantages of the process according to the invention include, for example, the fact that the reaction temperatures can be set lower than in conventional methods, and thus side reactions can be altogether reduced or even avoided.

The alkane is preferably an alkane that is gaseous under standard conditions, especially one selected from the group consisting of methane, ethane, propane or butane, or combinations thereof.

In another embodiment of the process according to the invention, the alkyl radical of the dialkylsulfonoyl peroxide (DASP) corresponds to the alkane employed in step c). This means that, if methane is employed as the alkane, then the dialkylsulfonoyl peroxide is dimethylsulfonoyl peroxide, and in the case of ethane, it is diethylsulfonoyl peroxide, etc.

In another embodiment of the process according to the invention, the temperature is set to from 25° C. to 65° C. in step b). Typically the temperature is set between 45 and 58° C.

In yet another embodiment of the process according to the invention, the pressure is set to from 40 bar to 110 bar in step c). Typically the pressure is 75-110 bar.

The duration in step e) may be from 3 hours to 7 days, in particular.

In the process according to the invention, it may be advantageous to dissolve the dialkylsulfonoyl peroxide (DASP) in an alkanesulfonic acid in step d), wherein the alkyl radical of the alkanesulfonic acid is the same as the alkyl radical in the dialkylsulfonoyl peroxide. In particular, the concentration of the DASP is from 1% by weight to 40% by weight, or from 1% by weight to 10% by weight. In the process according to the invention, the addition of the dialkylsulfonoyl peroxide (DASP) is typically effected at a flow rate of from 0.1 ml/min to 10 ml/min.

In the following, the invention is further illustrated in an exemplary way.

Under elevated pressure, methane reacts with sulfur trioxide and a free-radical initiator in a solvent to form methanesulfonic acid. Sulfur trioxide concentrations of from above 0 to 100% by weight may be employed. In particular, however, concentrations of from above 0 to 55%, especially of 20-55% by weight are employed. The reaction temperature depends on the free-radical initiator employed, and can be from 0° C. to more than 100° C. The pressure is proportional to the methane concentration in the solution and is to be set in accordance with the reaction conditions (sulfur trioxide concentration and free-radical initiator concentration, type of initiator), typically from 0.5 MPa (5 bar) to 12 MPa (120 bar). However, the reaction is also possible at higher or lower pressures. It is recommendable to purge the reactor with nitrogen in advance and afterwards with methane gas. All liquids should be degassed. All operations should be performed under inert conditions using a non-reactive gas to purge the whole apparatus before doing an experiment, e.g. nitrogen or a noble gas.

TABLE 1

Different SO$_3$-Concentration vs. the yield of Methanesulfonic acid

| SO$_3$-Konz./% | 41.9 | 36.3 | 35.0 | 32.7 | 29.4 |
|---|---|---|---|---|---|
| Ausbeute MSA/% | 87 | 92 | 96 | 88 | 30 |

TABLE 2

Effect of different Temperatures on the synthesis of Methanesulfonic acid

| Temperature/° C. | 60 | 55 | 50 | 40 |
|---|---|---|---|---|
| Ausbeute MSA/% | 62 | 93 | 94 | 46 |

TABLE 3

Effect of different pressures on the synthesis of Methanesulfonic acid.

| Druck/bar | 100 | 80 | 50 (konst.) | 15 | 10 |
|---|---|---|---|---|---|
| Ausbeute MSA/% | 92 | 97 | 99 | 69 | 47 |

The reaction is performed in a high-pressure autoclave. It may be operated as a stirred batch reactor, but also as a ((semi)continuous) flow reactor. The materials of the reactors are pressure-resistant alloys (for example, Hastelloy C, stainless steel 316, 316L). These are either stable towards the reaction conditions and the corrosive properties of the different substances, or lined with glass, plastics, ceramic or the like. For charging and metering the high-pressure reactor, either pressure-resistant cylinders or high-pressure pumps (for example, HPLC pumps) are employed. The methane consumption is controlled by a methane flow meter (constant pressure), or calculated from the pressure drop (constant volume). The measured data are sent through a controller to a computer for recording.

EXAMPLE

An HPLC pump (Knauer) is connected to a one-gallon (3.75 liters) high-pressure stainless steel reactor equipped with a glass liner, immersion tube, manometer, cooling coils, filling nozzles, agitator and rupture disk. Through a Swagelok cylinder, 947.4 g of oleum (24%, from Grillo-Werke AG, Frankfurt) is added to the reactor. Subsequently, the oleum is stirred with 100 revolutions per minute, and heated at 50° C. After the temperature is reached, the reactor is pressurized with 10 MPa (100 bar) of methane gas. Over 1 hour, the pressure drops by about 1 MPa (10 bar). Therefore, the methane is repeatedly replenished. After one hour, the pressure is constant, and the oleum is saturated with methane gas. Now, 100 ml of DMSP (bis(methanesulfonyl)peroxide) solution (about 5 g in 100 ml methanesulfonic acid) is slowly metered with the HPLC pump (1 ml/min). The pressure increases by about 0.25 MPa (2.5 bar). The temperature remains constant. Over 15 hours, the pressure drops to 8.3 MPa (83 bar). The pressure is released through a sulfuric acid scrubber down to 0.5 MPa (5 bar). The sample is removed under a slightly increased pressure. It is a clear colorless liquid that does not fume. This solution is directly examined by ion chromatography. A yield of more than 95% methanesulfonic acid is obtained (based on the sulfur trioxide employed). In the NMR spectrum and with ion chromatography, only sulfuric acid and methanesulfonic acid can be detected. The processing of the methanesulfonic acid is effected by distillation.

The invention claimed is:

1. A process for preparing alkanesulfonic acids from sulfur trioxide and an alkane, wherein sulfur trioxide, the alkane and dialkylsulfonoyl peroxide (DASP) react as components, the process comprising:
   a) sulfur trioxide as oleum with a sulfur trioxide concentration of from above 0% by weight to 55% by weight is charged in a high-pressure reactor in a condensed phase;
   b) a temperature of at least 25° C. is maintained in the high-pressure reactor;
   c) the gaseous alkane is introduced to the high-pressure reactor until a pressure of at least 10 bar is reached;
   d) dialkylsulfonoyl peroxide (DASP) is added into the high-pressure reactor; and
   e) after a duration of at least 5 hours, the produced alkanesulfonic acid is withdrawn.

2. The process according to claim 1, wherein said alkane is an alkane that is gaseous under standard conditions.

3. The process according to claim 1, wherein an alkyl radical of said dialkylsulfonoyl peroxide (DASP) corresponds to the alkane employed in step c).

4. The process according to claim 1, wherein the temperature is maintained from 25° C. to 65° C. in step b).

5. The process according to claim 1, wherein the pressure is from 4 MPa (40 bar) to 11 MPa (110 bar) in step c).

6. The process according to claim 1, wherein the duration in step e) is from 3 hours to 7 days.

7. The process according to claim 1, wherein said dialkylsulfonoyl peroxide (DASP) is added in step d) in an alkanesulfonic acid, wherein an alkyl of the alkanesulfonic acid is the same as that of the dialkylsulfonoyl peroxide.

8. The process according to claim 7, wherein the addition of the dialkylsulfonoyl peroxide (DASP) is at a flow rate of from 0.1 ml/min to 10 ml/min.

9. The process according to claim 2, wherein said alkane is selected from the group consisting of methane, ethane, propane or butane, or combinations thereof.

10. The process according to claim 7, wherein said dialkylsulfonoyl peroxide (DASP) is added in step d) in an amount of from 1% by weight to 10% by weight, with 100% by weight being the total amount of the alkanesulfonic acid and the DASP.

* * * * *